(12) United States Patent
Möhwald et al.

(10) Patent No.: US 6,197,922 B1
(45) Date of Patent: Mar. 6, 2001

(54) POLYSELENOPHENES, THE PREPARATION THEREOF AND THE USE THEREOF

(75) Inventors: Helmut Möhwald, Annweiler (DE); Vladimir Belov, St. Petersburg (RU); Wolfgang Schrof, Neuleiningen (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 09/149,446

(22) Filed: Sep. 9, 1998

(30) Foreign Application Priority Data

Sep. 10, 1997 (DE) .............................. 197 39 775

(51) Int. Cl.[7] .................................. C08G 65/00
(52) U.S. Cl. .............................. 528/403; 540/1; 548/120; 427/407.1
(58) Field of Search ................. 528/403; 540/1; 548/120; 427/407.1

(56) References Cited

FOREIGN PATENT DOCUMENTS

| 332 704 | 9/1989 | (EP) . |
|---|---|---|
| 97/32914 | 9/1997 | (WO) . |

OTHER PUBLICATIONS

Chem Abstract: 130:202690 "Polyselenophenes as materials with nonlinear optical properties" Wolfgang et al., Mar. 1999.*
113: 50973 "Polydihydroselenophenes and conductive charge transfer complexes" Fumis et al., Dec. 1989.*
Chem Abstracts: 109:161.360 "Extensively conjugated homologs of selenophene–TCNQ as new electron acceptors""Koji et al"; 85:143010 "Thieno–and selenolo [2,3–b]—and—[3,2–b] pyridines" Francis et al.; 125:312338 "Silver halide color photographic films having improved antistatic coatings" Noriki et al.*
125:301690 "Chemical and electrochemical polymerization of 3–alkyl selenophenes" Andrieu et al.*
108:120901 "Electrochemical polymerization of β substituted and β, β'–disubstituted selenophenes" Gerard et al.*
Arsalani et al., *J. Prakt. Chem.*, 37 (1995) pp. 1–11.

* cited by examiner

*Primary Examiner*—Duc Truong
(74) *Attorney, Agent, or Firm*—Keil & Weinkauf

(57) ABSTRACT

Novel polyselenophenes comprising one or more structural units of the formulae (I) or (II) or (I) and (II)

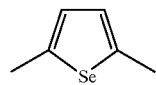

(I)

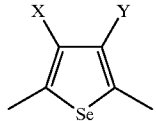

(II)

processes for preparing them, monomers for their preparation, their use in various technical sectors, and an electrically conducting material comprising them.

11 Claims, No Drawings

POLYSELENOPHENES, THE PREPARATION THEREOF AND THE USE THEREOF

The present invention relates to novel polyselenophenes; it relates further to processes and monomers for preparing polyselenophenes, to the use thereof in various industrial sectors, and to an electrically conducting material which comprises at least one polyselenophene according to the invention.

Polythiophenes are known inter alia as conjugated polymers with high electrical conductivity and nonlinear optical properties. They can be used as materials for semiconductors (see, inter alia, EP-B-0 332 704 and P. N. Prasad, D. J. Williams "Introduction to NLO effects in molecules and polymers", John Wiley and Sons, Inc. (1991)). The polythiophenes furthermore have electrochromic and antistatic properties (see N. Arsalani and K. E. Geckeler "Conducting isopolymers: preparation, properties, and applications", J. Prakt. Chem. 337 (1995) 1–11).

Further details of polythiophenes which can be used particularly well are to be found in PCT/EP97/01140 and the literature quoted therein.

Previously disclosed electrically conducting materials have not always been able to meet the increasing demands on these materials such as comparatively high electrical conductivity with, at the same time, good mechanical properties. These considerations show by way of example the need to develop novel, previously unknown doped and undoped poly- and oligomers.

It is an object of the present invention to provide novel polyselenophenes which can be used in various industrial areas in an advantageous manner as outlined above.

We have found that this object is achieved by the polyselenophenes according to the invention which are described in detail below.

The present invention thus relates to a polyselenophene comprising one or more structural units of the formulae (I) or (II) or (I) and (II)

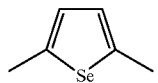
(I)

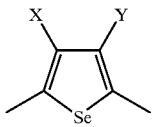
(II)

where

X and Y can be identical or different and, independently of one another, are hydrogen with the proviso that only one of X and Y is hydrogen; a linear or branched $C_1$–$C_{22}$-alkyl group; a linear or branched $C_1$–$C_{22}$-alkoxy group; a linear or branched $C_1$–$C_{22}$-alkyloxyalkyl group; a linear or branched $C_1$–$C_{22}$-acyl group; a linear or branched $C_1$–$C_{22}$-thioacyl group; a linear or branched $C_1$–$C_{22}$-acyloxy group; a linear or branched $C_1$–$C_{22}$-thioacyloxy group; a $C_5$–$C_8$-cycloalkyl group, a $C_6$–$C_{18}$-aryl group or a $C_5$–$C_8$-heterocyclic group, each of which in turn can be substituted by one or more linear or branched $C_1$–$C_{22}$-alkyl group(s), one or more linear or branched $C_1$–$C_{22}$-alkoxy group(s), one or more linear or branched $C_1$–$C_{22}$-alkyloxyalkyl group(s), one or more linear or branched $C_1$–$C_{22}$-acyl group(s) or one or more linear or branched $C_1$–$C_{22}$-thioacyl group(s); $NO_2$; or $NHR^1$ where $R^1$ can be identical or different and is in each case hydrogen, a linear or branched $C_1$–$C_{22}$-alkyl group, a linear or branched $C_1$–$C_{22}$-alkoxy group, a linear or branched $C_1$–$C_{22}$-alkyloxyalkyl group, a linear or branched $C_1$–$C_{22}$-acyl group or a linear or branched $C_1$–$C_{22}$-thioacyl group, or X and Y form, together with the atoms to which they are bonded, a carbon-containing ring system which, besides carbon, has nitrogen (N), oxygen (O), sulfur (S) or phosphorus (P) hetero atoms or mixtures of two or more of these hetero atoms, where this ring system can in turn be substituted on the carbon atom(s), the nitrogen atom(s) or the phosphorus atom(s) in each case by a group Z where Z is in each case, independently of one another, a group as defined above for X and Y, or two adjacent groups Z together form a radical depicted by the following formulae (III) to (VI)

(III)

(IV)

(IV)

(VI)

where A is carbon (C), nitrogen (N), phosphorus (P) or mixtures of two or more of these atoms, and in the case where A is carbon, each of these A either carries a hydrogen atom or can in turn be substituted as defined above for X and Y.

In another embodiment, the polyselenophene according to the invention comprises one or more thiophene structural units of the formulae (XII) or (XIII) or (XII) and (XIII)

(XII)

(XIII)

where

X and Y can be identical or different and, independently of one another, are defined as above for the polyselenophene units.

Preferred embodiments of the above thiophene units, and the preparation and properties of the corresponding compounds underlying these units, are to be found in the application PCT/EP97/01140 mentioned at the outset, which is in this regard incorporated in its entirety into the context of the present application.

The term "polyselenophene" as used in the present application comprises all poly- and oligomers which comprise one or more units of the formulae (I) and/or (II). This embraces both the presence of one or more identical units (I) and/or (II), and the presence of a plurality of different units (II), each of which can then in turn be present at least once in the polyselenophene according to the invention. The polyselenophenes according to the invention preferably comprise one or more units of the formulae (I) and (II). Also embraced are all poly- and oligomers which comprise one or more units of the formulae (I) and/or (II) together with one or more thiophene units of the formulae (XII) and/or (XIII).

Also embraced in addition are combinations of units of the formulae (I) and/or (II) with other conjugated organic structural units such as phenylene, biphenylene, terphenylene, naphthalene, anthracene, furan units, it being possible for these in turn to be mono- or polysubstituted as defined above for X and Y.

The structural unit (I) present in the polyselenophenes according to the invention is derived from selenophene.

In the structural unit (II), in which X and Y, if they do not form a carbon-containing ring system together with the atoms to which they are bonded, can in each case be the groups mentioned at the outset, it is preferred for X and Y to be identical. If X and Y are each the group $NHR^1$, the two $R^1$ radicals are preferably likewise identical. Among the alkyl, alkoxy, alkyloxyalkyl, acyl and thioacyl groups with 1 to 22 carbon atoms listed above, those with 1 to 20 are preferred, those with 6 to 20 carbon atoms are further preferred, and those with 10 to 16 carbon atoms are particularly preferred.

Particularly preferred substituents X and Y are the above-defined acyl groups, thioacyl groups and $NHR^1$.

The term "thioacyl group" means for the purpose of the present invention a group of the formula —C(S)—R where R is alkyl. The term "heterocyclic group" as mentioned at the outset means alicyclic saturated, alicyclic unsaturated and aromatic heterocyclic groups.

It is also possible for X and Y to form, together with the atoms to which they are bonded, a carbon-containing ring system which, besides carbon, has nitrogen (N), oxygen (O), sulfur (S) or phosphorus (P) hetero atoms or mixtures of two or more of these hetero atoms. In this case, X and Y preferably form a divalent radical which has two to eight atoms, furthermore preferably three to six atoms, and forms, together with the two atoms to which it is bonded, a ring system with four to ten or five to eight atoms. The number of the above-defined hetero atoms which may be present in this ring system is preferably up to three, furthermore preferably up to two. Among the above-defined hetero atoms, nitrogen (N) is preferred. The ring system described above is preferably a system having at least one, furthermore preferably two or more, double bonds. In particularly preferred embodiments of the present invention, the double bonds in the above ring system are conjugated with the double bonds in the selenophene fragment to which the ring system is bonded, and, where appropriate, with the double bonds in other radicals of the formulae (III) to (VI), as defined above which are bonded to the ring system described above.

This ring system may in turn be substituted on the carbon, nitrogen or phosphorus atoms in each case by one group Z where Z is in each case, independently of one another, a group as defined above for X and Y, and the substituents indicated as preferred for X and Y are in turn to be regarded as preferred here too.

Two adjacent groups Z may furthermore together form a radical which is selected from the radicals mentioned at the outset of the formulae (III) to (VI), where the spacers "A" are carbon (C), nitrogen (N), phosphorus (P) or mixtures of two or more of these atoms and, if A is carbon, the latter can either carry a hydrogen atom or in turn be substituted as defined above for X and Y. In this case, these radicals form together with the atoms to which they are bonded another ring which preferably forms a conjugated unsaturated system with the other rings within the structural unit.

A preferred ring produced in this way is the cyclobutene ring.

A preferred group of polyselenophenes according to the invention are those with structural units of the formulae (VII) and/or (VIII)

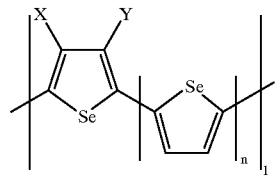

(VII)

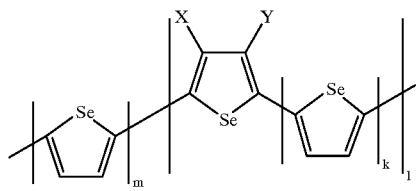

(VIII)

where X and Y are as defined above, and n, m and k are, independently of one another, an integer from 1 to 10, preferably an integer from 1 to 6, and 1 is an integer from 1 to 3000, preferably 1 to 1000, in particular 1 to 100. In this case, an alternating sequence of a substituted selenophene unit and an unsubstituted selenophene unit is preferred.

Polyselenophenes which are particularly preferred are those where the structural unit (II) is selected from the group consisting of the radicals of the following formulae (IIa) to (IIg)

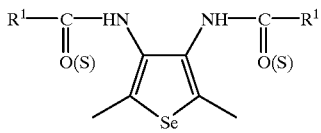

(IIa)

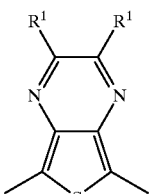 (IIb)

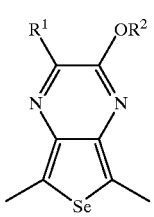 (IIc)

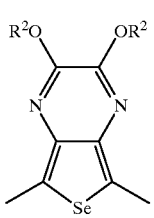 (IId)

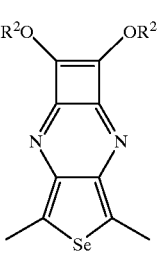 (IIe)

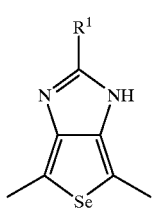 (IIf)

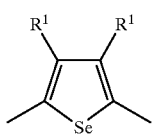 (IIg)

where $R^2=CH_2R^1$ or $R^2=CHR^1_2$, $R^1$=H or is as defined above.

Among the abovementioned structural units (II), the following individually listed structural units are particularly preferred. It is self-evident in this connection that these are derived from the corresponding disubstituted compounds in the vicinity of the selenophene selenium atom:

3,4-di(decyl)selenophene, 3,4-di(undecyl)selenophene, 3,4-di(dodecyl)selenophene, 3,4-di(tridecyl)selenophene, 3,4-di(tetradecyl)selenophene, 3,4-di(penta-decyl)selenophene, 3,4-di(hexadecyl)selenophene, 3,4-di(hepta-decyl)selenophene and 3,4-di(octadecyl)selenophene structural units;

3,4-di(decyloxy)selenophene, 3,4-di(undecyloxy)selenophene, 3,4-di(dodecyloxy)selenophene, 3,4-di(tridecyloxy)selenophene, 3–4-di(tetradecyloxy)selenophene, 3,4-di(pentadecyloxy)selenophene, 3,4-di(hexadecyloxy)selenophene, 3,4-di(heptadecyloxy)selenophene and 3,4-di(octadecyloxy)selenophene structural units; further preferred structural units are those where the above-defined ether residues are replaced by the corresponding thioether residues; 3,4-di(decyloxyethyl)selenophene, 3,4-di(undecyloxyethyl)selenophene, 3,4-di(dodecyloxyethyl) selenophene, 3,4-di(tridecyloxyethyl)selenophene, 3,4-di(tetradecyloxyethyl)selenophene, 3,4-di(pentadecyloxy-ethyl)selenophene, 3,4-di(hexadecyloxyethyl)selenophene, 3,4-di(heptadecyloxyethyl)selenophene and 3,4-di(octadecyloxyethyl)selenophene structural units;

and further preferred structural units are those where the oxygen atom(s) within the above-defined alkyloxyalkyl groups is (are) in, for example, position(s) 3, 3,6, 3,6,9, 3,6,9,12 etc., depending on the total length of the substituent, such as 3,4-di(2-ethyloxydecyl)-selenophene; 3,4-di(3-propyloxydecyl)selenophene; 3,4-di(4-butyloxydecyl)selenophene; 3,4-di(2-(2-(decyloxy)ethoxy)ethyl)selenophene; 3,4-di(2-(2-(undecyloxy)ethoxy)ethyl)selenophene; 3,4-di(2-(2-(dodecyloxy)ethoxy)ethyl)selenophene; etc., where the total number of carbon atoms does not exceed 22; further preferred structural units are those where the oxygen atom in the above-defined alkyloxyalkyl substituents is replaced by sulfur;

3,4-di(cyclopentyl)selenophene, 3,4-di(cyclo-pentenyl) selenophene, 3,4-di(cyclohexyl)selenophene, 3,4-di(cyclohexenyl)selenophene, 3,4-di(cyclohexadienyl) selenophene, 3,4-di(phenyl)selenophene and 3,4-di(benzyl)-selenophene structural units, where the abovementioned substituents can in turn be substituted by one or more of the groups defined for $R^1$;

3,4-di(decanoyl)selenophene, 3,4-di(undecanoyl)-selenophene, 3,4-di(dodeca-noyl)selenophene, 3,4-di(tridecanoyl)selenophene, 3,4-di(tetradecanoyl) selenophene, 3,4-di(pentadecanoyl)selenophene, 3,4-di(hexadecanoyl)selenophene, 3,4-di(heptadecanoyl) selenophene and 3,4-di(octadecanoyl)selenophene structural units; and the corresponding alkanoyloxy structural units such as 3,4-di(decanoyloxy) selenophene, 3,4-di(undecanoyloxy)selenophene, etc.; also preferred in this connection are substituents in which the carbonyl group present therein is replaced by a thiocarbonyl group;

3,4-di(decanoylamino)selenophene, 3,4-di(undecanoylamino)selenophene, 3,4-di(dodecanoylamino) selenophene, 3,4-di(tridecanoylamino)selenophene, 3,4-di(tetradecanoylamino)selenophene, 3,4-di(pentadecanoylamino)-selenophene, 3,4-di(hexadecanoylamino)selenophene, 3,4-di(heptadecanoylamino)selenophene and 3,4-di(octadecanoylamino)selenophene structural units, it also being possible in this case for the oxygen atom to be replaced by sulfur;

2,3-dipentylseleno[3,4-b]pyrazine, 2,3-didecylseleno-[3,4-b]pyrazine, 2,3-diundecylseleno[3,4-b]pyrazine, 2,3-didodecylseleno[3,4-b]pyrazine, 2,3-ditridecylseleno-[3,4-b]pyrazine, 2,3-ditetradecylseleno[3,4-b]pyrazine, 2,3-dipentadecylseleno[3,4-b]pyrazine, 2,3-dihexadecylseleno[3,4-b]pyrazine, 2,3- diheptadecylseleno[3,4-b]pyrazine and 2,3-dioctadecylseleno[3,4-b]pyrazine structural units;

2-methyl-3-decyloxyseleno[3,4-b]pyrazine, 2-methyl-3-undecyloxyseleno[3,4-b]pyrazine, 2-methyl-3-dodecyloxyseleno[3,4-b]pyrazine, 2-methyl-3-tridecyloxyseleno[3,4-b]pyrazine, 2-methyl-3-tetradecyloxy-seleno[3,4-b]pyrazine, 2-methyl-3-pentadecyloxy-seleno[3,4-b]pyrazine, 2-methyl-3-hexadecyloxyseleno[3,4b]pyrazine, 2-methyl-3-octadecyloxyseleno[3,4-b]pyrazine, 2-methyl-3-eicosyloxyseleno[3,4-b]pyrazine, 2-methyl-3-docosyloxyseleno[3,4-b]pyrazine, 2-ethyl-3-decyloxyseleno[3,4-b]pyrazine, 2-ethyl-3-undecyloxyseleno[3,4-b]pyrazine, 2-ethyl-3-dodecyloxyseleno[3,4-b]pyrazine, 2-ethyl-3-tridecyloxyseleno[3,4-b]pyrazine, 2-ethyl-3-tetradecyloxyseleno-[3,4-b]pyrazine, 2-ethyl-3-pentadecyloxyseleno-[3,4-b]pyrazine, 2-ethyl-3-hexadecyloxyseleno[3,4-b]pyrazine, 2-ethyl-3-octadecyloxyseleno-[3,4-b]pyrazine, 2-ethyl-3-eicosyloxyseleno[3,4-b]-pyrazine, 2-ethyl-3-docosyloxyseleno[3,4-b]pyrazine structural units, 2-phenyl-3-decyloxyseleno-[3,4-b]pyrazine, 2-phenyl-3-undecyloxyseleno[3,4-b]-pyrazine, 2-phenyl-3-dodecyloxyseleno[3,4-b]pyrazine, 2-phenyl-3-tridecyloxyseleno[3,4-b]pyrazine, 2-phenyl-3-tetradecyloxyseleno[3,4-b]pyrazine, 2-phenyl-3-pentadecyloxyseleno[3,4-b]pyrazine, 2-phenyl-3-hexadecyloxyseleno[3,4-b]pyrazine, 2-phenyl-3-heptadecyloxyseleno[3,4-b]pyrazine, 2-phenyl-3-octadecyloxyseleno[3,4-b]pyrazine, 2-phenyl-3-eicosyloxyseleno-[3,4-b]pyrazine and 2-phenyl-3-docosyloxyseleno-[3,4-b]pyrazine structural units, it also being possible in this case for the oxygen atom in the substituent to be replaced by sulfur;

2,3-di(decyloxy)seleno[3,4-b]pyrazine, 2,3-di(undecyloxy)seleno[3,4-b]pyrazine, 2,3-di(dodecyloxy)seleno[3,4-b]pyrazine, 2,3-di(tridecyloxy)seleno[3,4-b]pyrazine, 2,3-di(tetradecyloxy)seleno[3,4-b]pyrazine, 2,3-di(pentadecyloxy)seleno[3,4-b]pyrazine, 2,3-di(hexadecyloxy)seleno[3,4-b]pyrazine, 2,3-di(heptadecyloxy)seleno[3,4-b]pyrazine, 2,3-di(octadecyloxy)seleno-[3,4-b]pyrazine, 2,3-di(eicosyloxy)seleno[3,4-b]pyrazine and 2,3-di(docosyloxy)seleno[3,4-b]pyrazine structural units; further preferred structural units are those where the above-defined ether residues are replaced by the corresponding thioether residues;

2,3-di(decyloxyethyl)seleno[3,4-b]pyrazine, 2,3-di(undecyloxyethyl)seleno[3,4-b]pyrazine, 2,3-di(dodecyloxyethyl)seleno[3,4-b]pyrazine, 2,3-di(tridecyloxy-ethyl)seleno[3,4-b]pyrazine, 2,3-di(tetradecyloxyethyl)seleno[3,4-b]pyrazine, 2,3-di(pentadecyloxyethyl)seleno[3,4-b]pyrazine, 2,3-di(hexadecyloxyethyl)seleno[3,4-b]pyrazine, 2,3-di(heptadecyloxyethyl)seleno[3,4-b]pyrazine and 2,3-di-(octadecyloxyethyl)seleno[3,4-b]pyrazine structural units; further preferred structural units being those where the oxygen atom(s) within the above-defined alkyloxyalkyl groups is (are), for example, in position 3, 3,6, 3,6,9, 3,6,9,12 etc., depending on the total length of the substituent; such as 2,3-di(2-ethyloxydecyl)seleno[3,4-b]pyrazine; 2,3-di(3-propyloxydecyl)seleno[3,4-b]pyrazine; 2,3-di(4-butyloxydecyl)seleno[3,4-b]pyrazine etc.; 2,3-di(2-(2-(decyloxy)ethoxy)ethyl)seleno[3,4-b]pyrazine; 2,3-di(2-(2-(undecyloxy)ethoxy)ethyl)seleno[3,4-b]pyrazine; 2,3-di(2-(2-(dodecyloxy)ethoxy)ethyl)seleno[3,4-b]pyrazine etc., where the total number of carbon atoms does not exceed 22 in any case; further preferred structural units are those where the oxygen atom in the above-defined alkyloxyalkyl substituents is replaced by sulfur;

2,3-di(cyclopentyl)seleno[3,4-b]pyrazine, 2,3-di(cyclopentenyl)seleno[3,4-b]pyrazine, 2,3-di(cyclohexyl)seleno[3,4-b]pyrazine, 2,3-di(cyclohexenyl)seleno[3,4-b]pyrazine, 2,3-di(cyclohexadienyl)seleno[3,4-b]pyrazine, 2,3-di(phenyl)seleno[3,4-b]pyrazine and 2,3-di(benzyl)seleno-[3,4-b]pyrazine structural units, it being possible for the abovementioned substituents in turn to be substituted by one or more of the groups defined for $R^1$;

5,6-di(decyloxy)cyclobuta[b]seleno[3,4-e]pyrazine, 5,6-di(undecyloxy)cyclobuta[b]seleno[3,4-e]pyrazine, 5,6-di(dodecyloxy)cyclobuta[b]seleno[3,4-e]pyrazine, 5,6-di(tridecyloxy)cyclobuta[b]seleno[3,4-e]pyrazine, 5,6-di(tetradecyloxy)cyclobuta[b]seleno[3,4-e]pyrazine, 5,6-di(pentadecyloxy)cyclobuta[b]seleno[3,4-e]pyrazine, 5,6-di(hexadecyloxy)cyclobuta[b]seleno[3,4-e]pyrazine, 5,6-di(heptadecyloxy)cyclobuta[b]seleno[3,4-e]pyrazine and 5,6-di(octadecyloxy)cyclobuta[b]seleno[3,4-e]pyrazine structural units; further preferred structural units are those where the above-defined ether residues are replaced by the corresponding thioether residues;

5,6-di(cyclopentyloxy)cyclobuta[b]seleno[3,4-e]pyrazine, 5,6-di(cyclopentenyloxy)cyclobuta[b]seleno[3,4-e]-pyrazine, 5,6-di(cyclohexyloxy)cyclobuta[b]seleno-[3,4-e]pyrazine, 5,6-di(cyclohexenyloxy)cyclobuta[b]-seleno[3,4-e]pyrazine, 5,6-di(cyclohexadienyloxy)-cyclobuta[b]seleno[3,4-e]pyrazine, 5,6-di(phenyl)cyclobuta[b]seleno[3,4-e]pyrazine and 5,6-di(benzyl)cyclobuta[b]seleno[3,4-e]pyrazine structural units, it being possible for the abovementioned substituents in turn to be substituted by one or more of the groups defined for $R^1$;

2-decyl-1H-seleno[3,4-d]imidazole, 2-undecyl-1H-seleno[3,4-d]imidazole, 2dodecyl-1H-seleno[3,4-d]-imidazole, 2-tridecyl-1H-seleno[3,4-d]imidazole, 2tetradecyl1H-seleno[3,4-d]imidazole, 2-pentadecyl-1H-seleno[3,4-d]imidazole, 2-hexadecyl-1H-seleno[3,4-d]-imidazole, 2-heptadecyl-1H-seleno[3,4-d]imidazole and 2-octadecyl-1H-seleno[3,4-d]imidazole structural units;

2-cyclopentyl-1H-seleno[3,4-d]imidazole, 2-cyclopentenyl-1H-seleno[3,4-d]imidazole, 2-cyclohexyl-1H-seleno[3,4-d]-imidazole, 2-cyclohexenyl-1H-seleno[3,4-d]imidazole, 2-cyclohexadienyl-1H-seleno[3,4-d]imidazole, 2-phenyl-1H-seleno[3,4-d]imidazole and 2-benzyl-1H-seleno[3,4-d]-imidazole structural units; 2-butylthio-1H-seleno[3,4-d]-imidazole, 2-pentylthio-1H-seleno[3,4-d]imidazole, 2-hexylthio-1H-seleno[3,4-d]imidazole, 2-heptylthio-1H-seleno[3,4-d]imidazole, 2-octylthio-1H-seleno[3,4-d]imidazole, 2-nonylthio-1H-seleno[3,4-d]imidazole, 2-decylthio-1H-seleno[3,4-d]imidazole, 2-undecylthio-1H-seleno[3,4-d]imidazole, 2-dodecylthio-1H-seleno[3,4-d]-imidazole, 2-tridecylthio-1H-seleno[3,4-d]imidazole, 2-tetradecylthio-1H-seleno[3,4-d]imidazole, 2-pentadecylthio-1H-seleno[3,4-d]imidazole, 2-hexadecylthio-1H-seleno[3,4-d]imidazole, 2-heptadecylthio-1H-seleno[3,4-d]imidazole, 2-octadecylthio-1H-seleno[3,4-d]-imidazole structural units, it being possible for the abovementioned substituents in turn to be substituted by one or more of the groups defined for $R^1$.

The proportions of the above-defined structural units (I) and (II) in the polyselenophenes according to the invention is from about 1 to about 99 mol % (I) and from about 99 to about 1 mol % (II), preferably from about 30 to about 70 mol % (I) and from about 70 to about 30 mol % (II), and in particular about 50 mol % (I) and about 50 mol % (II), where the proportions of these two structural units in each case add up to 100 mol %. There is preferably an alternating sequence of the two structural units (I) and (II).

The weight average molecular weight ($M_w$) of the polyselenophenes prepared according to the invention, measured by gel permeation chromatography using polystyrene as standard, is generally from about 1000 to about 500,000, preferably from about 10,000 to about 250,000, and in particular from about 30,000 to about 80,000. The inhomogeneity of the molecular weight distribution, ie. the ratio of the weight average molecular weight and the number average molecular weight ($M_w/M_n$), is from about 2 to about 4, preferably from about 2 to about 3, and in particular from about 2 to about 2.5.

The polyselenophenes according to the invention can be polymerized by all reactions suitable for polymerizing pyrroles or thiophenes, eg. by chemical or electrochemical oxidation; some of the polyselenophenes which have, for example, alkyl, alkoxy, acylamino or alkyloxyalkyl substituents can also be reacted by catalytic coupling of organometallic reagents (usually Grignard reagents). For details of this reaction, reference is made to PCT/EP97/01140 mentioned in the introduction, and the literature referred to therein.

The preferred processes for preparing the polyselenophenes according to the invention are, however, the Stille reaction and the Suzuki reaction (see A. Suzuki et al. "Stereoselective synthesis of arylated (E)-alkanes by the reaction of alk-1-enylboranes with aryl halides in the presence of palladium catalyst", J. C. S. Chem. Comm. 1979, 866–867), which will be explained in detail below.

In the Suzuki reaction, 2,5-dihalo- or 2,5-triflate-substituted selenophenes which correspond to the structural unit (II) used according to the invention are reacted with selenophenediboric acid or selenophenediboric esters in the presence of a base, preferably sodium methoxide, and a palladium complex of the structure $PdL_4$ (L=ligand), preferably $Pd(PPh_3)_4$.

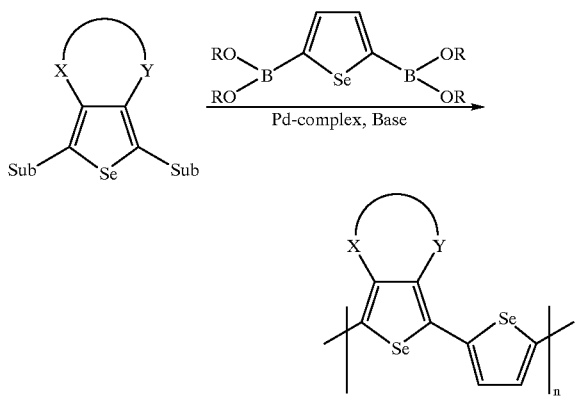

Sub = halogen or triflate
X, Y = as defined above
R = H or alkyl

The preferred boranes employed in this reaction are selenophene-2,5-diboric acid and its esters. For further details of this reaction, reference is made to the reference cited above.

It is, of course, possible in the Suzuki reaction to react the diboric acid (ester) derivatives of the selenophene derivatives, corresponding to the above structural units (II) with 2,5-dihalo or 2,5-triflate-substituted selenophene which corresponds to the structural unit (I).

However, the particularly preferred process for preparing the polyselenophenes according to the invention is the Stille reaction mentioned at the outset. In this reaction, 2,5-dihaloselenophene or 2,5-ditriflatoselenophene and selenophene derivatives which are bis(trialkyltin)-substituted on the carbon atoms adjacent to the selenium and which correspond to the above-defined structural unit (II), or 2,5-bis(trialkyltin)selenophene and selenophene derivatives which are bis(halo)- or bis(triflate)-substituted on the carbon atoms adjacent to the selenium and which correspond to the above-defined structural unit (II), are reacted together as shown in the following scheme in suitable solvents in the presence of suitable Pd(0) or Pd(II) complexes or salts as catalyst.

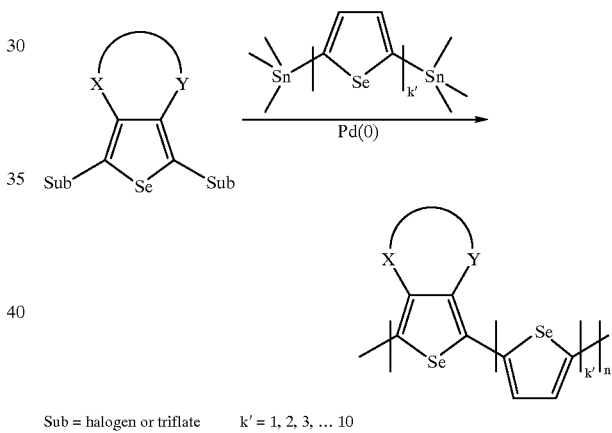

Sub = halogen or triflate    k' = 1, 2, 3, ... 10

Among the substituents "Sub" mentioned in the above scheme, halogen-substituted derivatives are preferably employed. Where bis(triflate), ie. ($CF_3SO_3$)-substituted precursors are employed, it is possible to add, for example, LiCl to improve the reactivity.

Because of the mild conditions for carrying out this reaction, all types of substituents are tolerated, such as amine, acyl, ester, ether and nitro groups.

Pd(II) or Pd(0) complexes are employed as catalysts. Particularly preferred catalysts are the following: tris(dibenzylideneacetone)dipalladium ($Pd_2dba_3$), $Pd(Ph_3P)_2Cl_2$ where Ph is $C_6H_5$, and $Pd(Ph_3P)_4$. When tris(dibenzylideneacetone)dipalladium is used, various ligands (L) can be added to form the catalytically active catalyst $PdL_4$ in situ by ligand exchange between the weakly coordinated $Pd_2dba_3$ and the ligand(s). Ligands used in this case are $PPh_3$, $AsPh_3$, $[2-(CH_3)C_6H_4]_3P$, $P(OPh)_3$ and $(2-furyl)_3P$. The amount of catalyst employed is from about 2 to about 10 mol %, preferably from about 2 to about 5 mol %, based on the amount of the bis(trialkyltin)-substituted precursor employed.

Although it is possible in general to employ all solvents able to keep the precursors and catalysts in solution, the most suitable solvents are DMF, NMP and cyclic ethers such as THF and dioxane. Among these, DMF and THF are preferably employed.

The reaction is generally carried out at temperatures from room temperature to the boiling point of the solvent, with temperatures from about 50° C. to about 100° C. being preferred. The reaction time depends on the precursors and/or catalysts used and is from 1 day to 1 month, preferably 1 day to 1 week.

A similar procedure is used for preparing copolymers or cooligomers with thiophene and/or other conjugated organic units.

It is possible by this relatively mild reaction to prepare polyselenophenes with the following advantageous properties:

The resulting selenophenes display only slight or no structural defects, doping or overoxidation;

it is possible to insert a large number of functional groups, including acceptors, donors and π systems with a plurality of bonds between carbon and a hetero atom; and it is possible to obtain strictly alternating copolyselenophenes with differently substituted rings, for example to carry out the reaction of selenophenes substituted in position 3 and 4 with unsubstituted selenophenes, which has been possible only with extreme difficulty with the processes generally used to date for preparing polyselenophenes.

Although the Suzuki reaction also displays the above-mentioned advantages by comparison with conventional methods, the Stille reaction is particularly preferred for the purpose of the present invention because it differs from the Suzuki reaction in not requiring additional base.

The present invention furthermore provides compounds of the formulae (IXa) to (IXc)

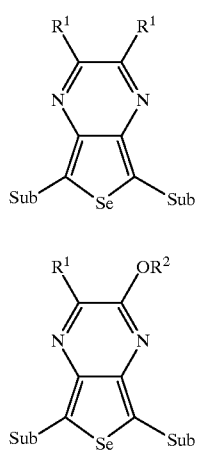

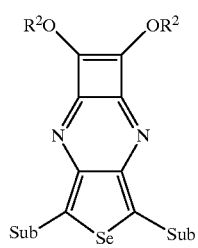

where Sub is hydrogen (H), bromine (Br), chlorine (Cl), iodine (I), triflate ($CF_3SO_3$) or trialkyltin, and $R^1$ is as defined above, and $R^2$ is $CH_2R^1$ or $CHR^1_2$.

Also provided are N,N-substituted 3,4-diamino-2,5-disubstituted (preferably dihalo or ditriflato)selenophenes of the formula (X)

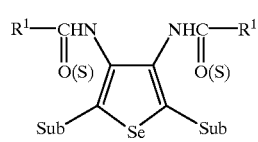

where Sub and $R^1$ are as defined above.

Preferred substitutents Sub are the abovementioned halo radicals, with further preference for iodine or bromine. Concerning preferred radicals $R^1$, reference is made to the listing given hereinbefore.

Although this class of monomers can in general be prepared by conventional processes for preparing such compounds, the general process explained in the examples is preferably used to prepare the monomers according to the invention.

Another aspect of the present invention represents the provision of 2,5-bis(trialkyltin)selenophene (formula XIa), 5,5'-bis(trialkyltin)-2,2'-diselenophene (formula XIb) and the 5,5"-bis(trialkyltin)-2,2':5',2"-terselenophene of the formula (XIc), and the 2-(trialkyl-tin)selenophene (formula XId), each of which can likewise be used for synthesizing oligo- and polyselenophenes,

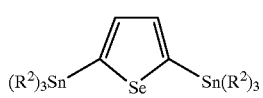

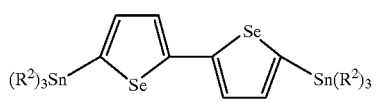

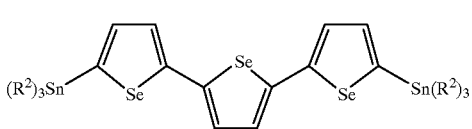

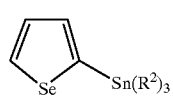

where $R^2$ is an alkyl group, preferably a methyl or butyl group. Preparation of these selenophenes is described in the examples.

Further provided according to the invention are the dimer and trimer of selenophene, ie. 2,2'-biselenophene and 2,2':5', 2"-terselenophene.

Thin films of the polyselenophenes used according to the invention can be produced by pouring carefully filtered or centrifuged solutions in chloroform or trichloroethylene onto a glass substrate. It is possible by this process to obtain homogeneous films with a thickness of up to 300 nm. The optical quality of the films is high with negligible light scattering.

The polyselenophenes described herein can be used either undoped or doped for application as antistatic to substances which conduct electric current only poorly or not at all, as electrically conducting sheets, as semiconductor sheets, as additive to active electrodes, for LEDs, as organic transistors and capacitors. For this purpose these copolymers are processed in a conventional way and, where appropriate, mixed with known additives and formulating substances necessary for the particular use, and processed by known processes.

The present invention further provides an electrically conducting sheet, a semiconductor sheet, a LED, an organic transistor, a capacitor, an active electrode, each comprising at least one of the polyselenophenes as defined herein.

The present invention furthermore provides a process for applying antistatic to a substrate which conducts electric current only poorly or not all by application of a layer comprising an electrically conducting organic polymer to the surface of the substrates, wherein a layer of at least one polyselenophene which comprises the above-defined structural units of the formulae (I) and/or (II) is produced on the surface of the substrate by polymerization. This layer mentioned above may moreover consist exclusively of the conducting organic polymer defined above.

The present invention further provides an electrically conducting material which comprises at least one polyselenophene of the present invention.

The present invention is now to be illustrated further by some selected examples.

EXAMPLES

Example 1

2,5-Bis(trimethyltin)selenophene (A) was obtained directly starting from selenophene 1 via the 2,5-dilithium derivative 2. Compound 2 was prepared as described by B. J. Wakefield, "Organolithium methods", Academic Press, 1988, pages 47–48 (of the Russian translation) and the literature cited therein, in which the reaction is described for the corresponding thiophene, by reaction with BuLi/hexane with TMEDA under reflux. The reaction is illustrated by Scheme 1 below:

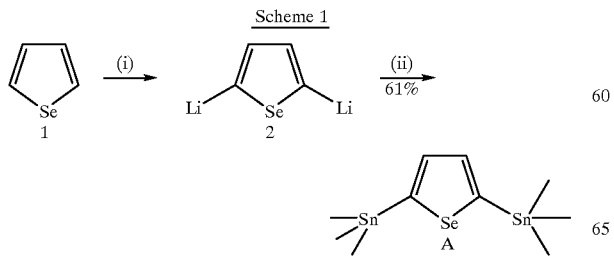

-continued
i: 2.5 equivalents of BuLi/TMEDA; hexane, reflux
ii: (CH₃)₃SnCl, hexane, 0° C., room temperature An analytically pure sample of compound A was obtained after recrystallization from hexane twice. The structure (and purity) of compound A was confirmed by $^1$H-NMR spectroscopy.

Compound A had a melting point of 123 to 124° C. (hexane).

$^1$H-NMR(200 MHz, CDC$_3$, δ, ppm): 0.38 s (CH$_3$), 0.38 d (CH$_3$, J($^{117}$Sn—$^1$H)=J($^{119}$Sn—$^1$H)=56.7 Hz), total intensity of the two signals: 9H), 7.70 s (H$^{a'}$); due to spin-spin coupling ($^3$J) with $^{117}$Sn/$^{119}$Sn and $^{77}$Se, a symmetrical multiplet at about 7.70 ppm with a total intensity corresponding to 1H was observed.

Example 2

The 2,2'-biselenophene 6 was obtained starting from 2-iodoselenophene 3 and 2-(trimethyltin)selenophene 5. 2-Iodoselenophene was obtained as described in Yurjev et al., Russ. J. of General Chem., 26 (1956), 3154.

2-(Trimethyltin)selenophene 5 was obtained by quenching 2-lithiumselenophene with trimethyltin chloride. The monolithium derivative was obtained selectively starting from selenophene by reaction of one equivalent of butyllithium in hexane in the presence of TMEDA (N,N,N',N'-tetramethylethylenediamine).

The Stille reaction between 2-iodo- and 2-(trimethyltin) selenophene provided the dimeric 2,2'-biselenophene 6 as main product. The yield of compound 6 after purification on silica gel and removal of the trimer 9 was 69% based on the amount of compound 3 employed.

The reaction described above is explained again in Scheme 2 below. Compound 6 has a melting point of 36–38° C. (hexane).

$^1$H-NMR (200 MHz, CDCl$_3$, δ, ppm): 7.3 m (2H, H$^b$+H$^c$), 7.94 d (1H, H$^a$, J$_{ab}$ 4.5 Hz); a doublet of doublets (dd) of low intensity centered on 7.94 ppm was also observed, $^2$J($^{77}$Se—H)=47 Hz, J$_{ab}$=5.4 Hz, integrated intensity of this dd: 6% of the intensity of the main signal, which corresponds to the natural content of $^{77}$Se (7.6).

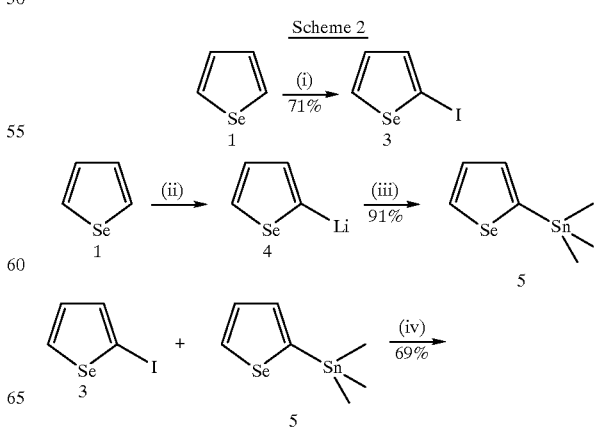

15

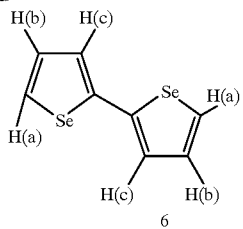

i: I₂/HgO, benzene
ii: BuLi/TMEDA, hexane, 0° C. - room temperature (RT)
iii: (CH₃)₃SnCl, hexane, 0° C - RT
iv: 5 mol% Pd(Ph₃P)₂Cl₂, THF, reflux As shown in the lower part of Scheme 3, compound 6 was obtained once again starting from 2-bromoselenophene 7, which was prepared as described by H. Suginome, S. Umezawa, Bull. Chem. Soc., 11 (No. 3), (1936) 157–167, in a yield of about 20% based on the amount of compound 7 employed.

Scheme 3

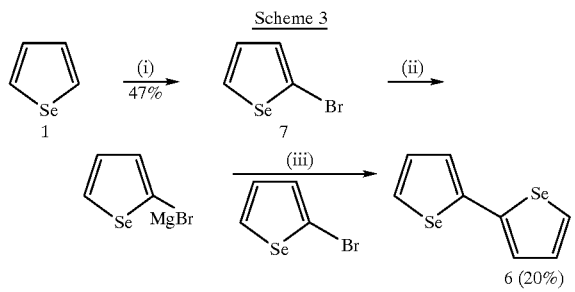

i: Br₂/Cs₂, 0° C. - RT
ii: Mg, THF, reflux
iii: Ni(dppp)Cl₂, THF, reflux

Example 3

The 2,2':5',2"-terselenophene 9 was obtained starting from 2-iodoselenophene 3 and 2,5-bis(trimethyltin)selenophene A as shown in Scheme 4 below Scheme 4

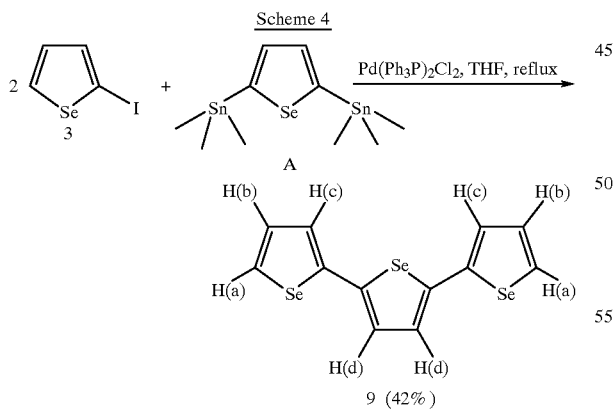

Compound 9 was obtained in a yield of 42% and purified on silica gel. Compound 9 had a melting point of 169–171° C.

¹H-NMR(200 MHz, CDCl₃, δ, ppm): 7.14 s (2H, H$^d$), 7.24 m (4H, H$^b$+H$^c$), 7.88 d (2H, H$^a$, J$_{ab}$ 5 Hz); a doublet of doublets (dd) of low intensity centered on 7.88 ppm was also observed, ²J($^{77}$Se—H)=47 Hz, J$_{ab}$=6.3 Hz.

16

Subsequent conversion of compound 9 into compound C was carried out as shown in Scheme 5 below, and compound C was obtained in a yield of 24% based on the starting compound 9. To purify the resulting reaction product, it was washed with cold pentane. Compound C decomposes on heating at about 70° C.

¹H-NMR (200 MHz, CDCl₃, δ, ppm): 0.38 s (CH³), 0.38 d (CH₃, J($^{117}$Sn—¹H)=J$^{119}$Sn—¹H)=56.3 Hz), total intensity of the two signals: 18H), 7.13 s (2H, H$^c$), 7.32 d (2H, H$^a$/H$^b$, J 3.6 Hz), 7.37 d (2H, H$^b$/H$^a$, J 3.6 Hz).

Scheme 5

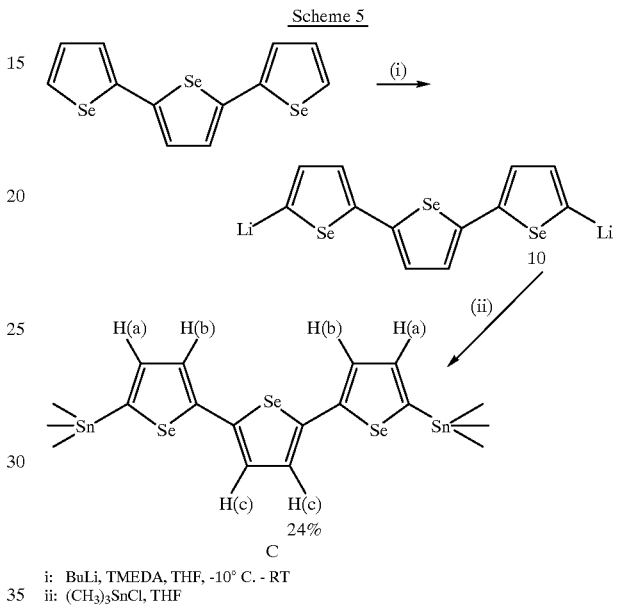

i: BuLi, TMEDA, THF, -10° C. - RT
ii: (CH₃)₃SnCl, THF

Example 4

2,5'-Bis(trialkyltin)-5,2'-diselenophene (B)

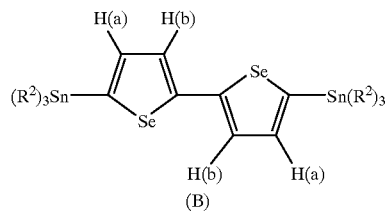

was prepared as in Example 3 starting from 2,2'-biselenophene 6 in the same way as indicated for the trimer C in Scheme 5.

Compound B had a melting point of 113–115° C. (hexane).

¹H-NMR (200 MHz, CDCl₃, δ, ppm): 0.38 s (CH₃), 0.38 d (CH₃, J($^{117}$Sn—¹H)=J($^{119}$Sn—¹H)=56.2 Hz), total intensity of the two signals: 9H), 7.36 m (2H, H$^{a''}$)

We claim:
1. A polyselenophene comprising one or more structural units of the formulae (II) or (I) and (II)

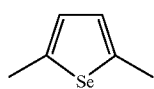
(I)

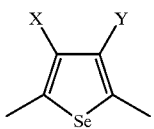
(II)

where
- X and Y can be identical or different and, independently of one another, are hydrogen with the proviso that only one of X and Y is hydrogen; a linear or branched $C_1$–$C_{22}$-alkyl group; a linear or branched $C_1$–$C_{22}$-alkoxy group; a linear or branched $C_1$–$C_{22}$-alkyloxyalkyl group; a linear or branched $C_1$–$C_{22}$-acyl group; a linear or branched $C_1$–$C_{22}$-thioacyl group; a linear or branched $C_1$–$C_{22}$-thioacyloxy group; a linear or branched $C_1$–$C_{22}$-acyloxy group; a $C_5$–$C_8$-cycloalkyl group, a $C_6$–$C_{18}$-aryl group or a $C_5$–$C_8$-heterocyclic group, each of which in turn can be substituted by one or more linear or branched $C_1$–$C_{22}$-alkyl group(s), one or more linear or branched $C_1$–$C_{22}$-alkoxy group(s), one or more linear or branched $C_1$–$C_{22}$-alkyloxyalkyl group(s), one or more linear or branched $C_1$–$C_{22}$-acyl group(s) or one or more linear or branched $C_1$–$C_{22}$-thioacyl group(s); $NO_2$; or $NHR^1$ where $R^1$ can be identical or different and is in each case hydrogen, a linear or branched $C_1$–$C_{22}$-alkyl group, a linear or branched $C_1$–$C_{22}$-alkoxy group, a linear or branched $C_1$–$C_{22}$-alkyloxyalkyl group, a linear or branched $C_1$–$C_{22}$-acyl group or a linear or branched $C_1$–$C_{22}$-thioacyl group, or X and Y form, together with the atoms to which they are bonded, a carbon-containing ring system which, besides carbon, has nitrogen (N), oxygen (O), sulfur (S) or phosphorus (P) hetero atoms or mixtures of two or more of these hetero atoms,
- where this ring system can in turn be substituted on the carbon atom(s), the nitrogen atom(s) or the phosphorus atom(s) in each case by a group Z where Z is in each case, independently of one another, a group as defined above for X and Y, or
- two adjacent groups Z together form a radical depicted by one of the following formulae (III) to (VI)

(III)

(IV)

(IV)

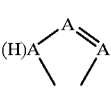
(VI)

where A is carbon (C), nitrogen (N), phosphorus (P) or mixtures of two or more of these atoms, and in the case where A is carbon, each of these A either carries a hydrogen atom or can in turn be substituted as defined above for X and Y which polyselenophene is prepared by the Stille reaction, wherein 2,5-dihaloselenophene or 2,5-ditriflateselenophene and selenophene derivatives which are bis(trialkyltin)-substituted on the carbon atoms adjacent to the sulfur, which correspond to the structural unit (II) defined above, or 2,5-bis(trialkyltin)selenophene and selenophene derivatives which are bis(halo)- or bis (triflate)-substituted on the carbon atoms adjacent to the sulfur, which correspond to the structural unit (II) defined above, are reacted with one another in suitable solvents in the presence of suitable Pd(0) or Pd(II) complexes or salts thereof as catalyst, or the Suzuki reaction, wherein 2,5-dihalo- or 2,5-triflate-substituted selenophenes which correspond to the structural unit (II) according to the invention, are reacted with selenophenediboric acid or selenophene-diboric acid esters in the presence of a base of a palladium complex of the structure $PdL_4$ (L=ligand), or wherein the diboric acid (ester) derivatives of the derivatives corresponding to the above structural units (II) are reacted with 2,5-dihalo- or 2,5-triflate-substituted selenophene in the presence of a base and a palladium complex, as defined above, or by said Stille or said Suzuki reaction, which is carried out between two kinds of suitably substituted selenophene derivatives corresponding to the structural unit (II).

2. A polyselenophene comprising structural units of the formulae (VII) or (VIII)

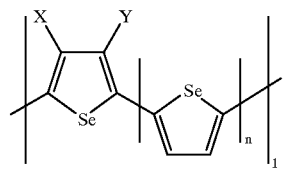
(VII)

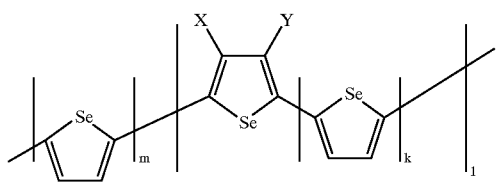
(VIII)

where X and Y are as defined in claim 1, n, m and k are each, independently of one another, an integer from 1 to 10, and l is an integer from 1 to 3000.

3. A polyselenophene where the structural unit is selected from the group consisting of the radicals of the following formulae (IIa) to (IIg)

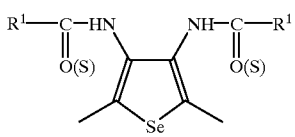
(IIa)

-continued (IIb)
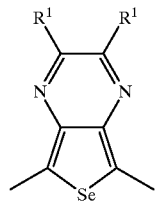

(IIc)
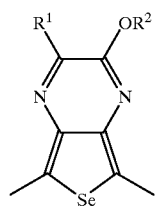

(IId)
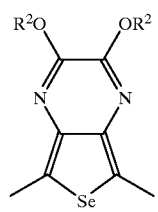

(IIe)
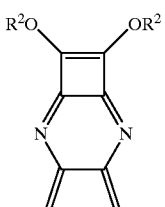

(IIf)
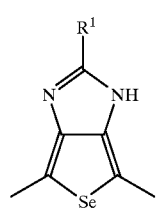

(IIg)
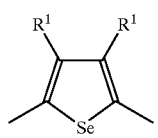

and mixtures thereof, where $R^1$ is as defined as in claim 1, and $R^2$ is $CHR^1_2$ or $CH_2R^1$.

4. A compound of the formula (IXa), (IXb) or (IXc)

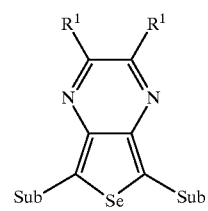
IXa

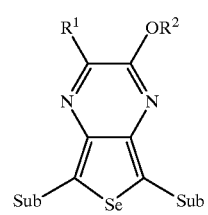
IXb

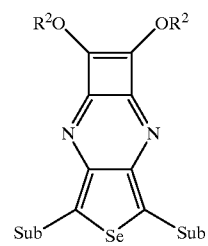
IXc where Sub is hydrogen (H), bromine (Br), chlorine (Cl), iodine (I), triflate ($CF_3SO_3$) or trialkyl tin and $R^1$ is as defined in claim 1, and $R^2$ is $CHR^1_2$ or $CH_2R^1$.

5. An N,N-substituted 3,4-diamino-2,5-disubstituted selenophene of the formula (X)

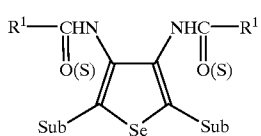
(X)

where Sub is as defined in claim 4 and $R^1$ is as defined in claim 1.

6. A 2,5-bis(trialkyltin)selenophene of the formula (XIa)

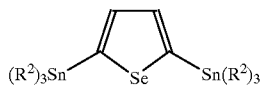
(XIa)

2,5'-bis(trialkyltin)-5,2'-diselenophene of the formula (XIb)

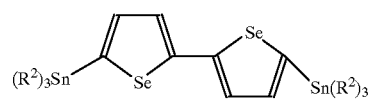
(XIb)

5,5"-bis(trialkyltin)-2,2':5',2"-terselenophene of the formula (XIc)

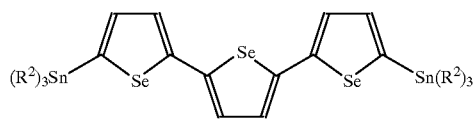
(XIc)

2-(trialkyltin)selenophene of the formula (XId)
where $R^2$ is in formulas (XIa) (XIb) and (XIc) and a methyl group in formula (XId) an alkyl group; 2,2'-biselenophene or 2,2':5',2"-terselenophene

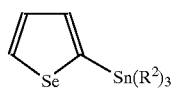
(XId)

7. A process for preparing a polyselenophene, wherein 2,5-dihaloselenophene or 2,5-ditriflatoselenophene and selenophene derivatives which are bis(trialkyltin)-substituted on the carbon atoms adjacent to the selenium and which correspond to the structural unit (II) defined in claim 1 are reacted together in suitable solvents in the presence of suitable Pd(0) or Pd(II) complexes as catalyst.

8. A process for preparing a polyselenophene, wherein 2,5-bis(trialkyltin)selenophene and selenophene derivatives which are bis(halo)- or bis(triflate)-substituted on the carbon atoms adjacent to the selenium and which correspond to the structural unit (II) defined in claim 1 are reacted together in suitable solvents in the presence of suitable Pd(0) or Pd(II) complexes as catalyst.

9. A process for applying antistatic to a substrate which conducts electric current only poorly or not at all by application of a layer comprising an electrically conducting organic polymer to the surface of the substrate, wherein a layer of at least one polyselenophene which comprises one or more structural units of the formulae (I) or (II) or (I) and (II) as defined in claim 1 is produced on the surface of the substrate by polymerization.

10. An electrically conducting material comprising at least one polyselenophene as claimed in claim 1.

11. Electrically conducting sheet, a semiconductor sheet, a LED, an organic transistor, a capacitor, an active electrode, each comprising at least one of the polyselenophenes as claimed in claim 1.

* * * * *